US006407056B1

(12) United States Patent
Seiberg et al.

(10) Patent No.: US 6,407,056 B1
(45) Date of Patent: *Jun. 18, 2002

(54) METHODS FOR ALTERING HAIR GROWTH AND HAIR PIGMENTATION BY APOPTOSIS IN THE FOLLICULAR PAPILLAE AND COMPOSITIONS THEREFOR

(75) Inventors: Miri Seiberg, Princeton; Stanley S. Shapiro, Livingston; Gerard F. M. J. Cauwenbergh, Plainsboro, all of NJ (US); Stephen J. Wisniewski, Doylestown, PA (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/882,322

(22) Filed: Jun. 25, 1997

Related U.S. Application Data
(60) Provisional application No. 60/021,629, filed on Jul. 12, 1996.

(51) Int. Cl.$^7$ .............................................. A61K 38/00
(52) U.S. Cl. .......................... 514/2; 514/880; 530/350; 424/70.01; 424/70.14; 424/70.6; 424/78.02; 424/94.64
(58) Field of Search ................................ 530/350; 514/2, 514/880; 424/70.1, 70.14, 70.6, 78.02, 94.64

(56) References Cited

U.S. PATENT DOCUMENTS

| 1,602,163 A | | 10/1926 | Monti | |
| 2,930,736 A | | 3/1960 | Sullivan et al. | 167/73 |
| 2,973,300 A | | 2/1961 | Farrar et al. | |
| 2,978,385 A | | 4/1961 | Damaskus | 195/63 |
| 3,003,917 A | | 10/1961 | Beiler et al. | 167/73 |
| 3,050,445 A | | 8/1962 | Damaskus | 195/63 |
| 3,860,702 A | | 1/1975 | Buell | 424/94 |
| 3,940,478 A | | 2/1976 | Kurtz | 424/94 |
| 4,740,372 A | | 4/1988 | Boncic | 424/94 |
| 5,068,315 A | * | 11/1991 | Buultjens et al. | 530/324 |
| 5,095,007 A | | 3/1992 | Ahluwalia et al. | 514/23 |
| 5,096,911 A | | 3/1992 | Ahluwalia et al. | 514/380 |
| 5,132,293 A | | 7/1992 | Shander et al. | 514/46 |
| 5,133,968 A | * | 7/1992 | Nakayama et al. | 424/401 |
| 5,143,925 A | | 9/1992 | Shader et al. | 514/378 |
| 5,230,891 A | * | 7/1993 | Nakayama et al. | 424/401 |
| 5,296,222 A | | 3/1994 | Petersen et al. | 424/94 |
| 5,439,935 A | * | 8/1995 | Rawlings | 514/451 |
| 5,455,234 A | | 10/1995 | Ahluwalia et al. | 514/46 |
| 5,468,476 A | | 11/1995 | Ahluwalia et al. | 424/73 |
| 5,498,603 A | | 3/1996 | Clodman et al. | 514/25 |

FOREIGN PATENT DOCUMENTS

| EP | 0 079 074 | | 5/1983 |
| EP | 0079074 | * | 5/1983 |
| FR | 2729079 | * | 7/1996 |
| WO | WO93/25694 | | 12/1993 |
| WO | WO 96/25946 | | 8/1996 |
| WO | WO 95124181 | | 9/1996 |

OTHER PUBLICATIONS

Protopapa et al., Epitheor. Klin. Farmakol. Farmakokinet., Int. Ed. 8(2), 84–8, 1994.*
Protopapa et al., Epitheor. Klin. Farmakol. Farmakokinet., Int. Ed., 8(2), 84–8.(Abstract), 1994.*
120(7) Chem. Abstracts #75653 (Feb. 14, 1994) of JP 05276939A (Oct. 1993).
Database Medline Abstract of Seiberg, et al. 208(4) Dev. Dynamics 553–64 (Apr., 1997), AN: 97251345.
Santulli, et al., "Evidence for the Presence of a Protease–Activated Receptor Distinct From the Thrombin Receptor in Human Keratinocytes". Proc. Natl. Acad. Sci. USA vol. 92, pp. 9151–9155, Sep. ('95).
"Hair Follicle Growth Controls," Dermatologic Clinics vol. 14, No. 4 (10/96) Kurt S. Stenn, MD et al.pp. 543–558.
"Changes In Expression of Apoptosis–Associated Genes in Skin Mark Early Catagen," Miri Seiberg, et al., 104 (1) The Journal of Investigative Dermatology, Inc. pp 78–82.
Marthinuss, et al., "A Secreted Serine Protease Can Induce Apoptosis in Pam212 Keratinocytes," vol. 6, pp. 807–816, Jul. 1995.
"Apoptosis in Pam212, an Epidermal Keratinocyte Cell Line: A Possible Role for bcl–2 in Epidermal Differentiation," vol. 6, 239–250,(Mar. 1995), Cell Growth & Differentiation, Jeffrey Marthinuss, et al.
"Expression of the bcl–2 Protooncogene in the Cycling Adult Mouse Hair Follicle," K. S. Stenn, et al., 103 (1) The Journal of Investigative Dermatology, pp. 107–111 (1994).
Trypsin–Induced Follicular Papilla Apoptosis Results in Delayed Hair Growth and Pigmentation Developmental Dynamics 208:553–564 (1997) M. Seiberg, et al.
"The Biochemistry of Programmed Cell Death," Guido Kroemer, et al., Reviews, as cited in 9 FASEB J. 1277–87 (1995).
"Hair Follicle Stem Cells: Their Location, Role in Hair Cycle, and Involvement in Skin Tumor Formation," Robert M. Lavker, et al., pp 16S–26S, 101 (1) Journal of the Investigative Dermatology (Supp. Jul. 1993).

(List continued on next page.)

*Primary Examiner*—Dwayne C. Jones
*Assistant Examiner*—C. Delacroix-Muirheid (57) ABSTRACT

The present invention utilizes serine proteases and their ability to induce programmed cell death and apoptosis in the follicular papillae to affect changes in mammalian hair growth and hair pigmentation. Also described are compositions which have an agent with a portion of similar structure to a portion of the trypsin molecule, allowing said agent to induce programmed cell death and apoptosis in the same manner as trypsin.

17 Claims, 5 Drawing Sheets

(1 of 5 Drawing Sheet(s) Filed in Color)

OTHER PUBLICATIONS

"The Control of Hair Growth: An Overview," Andrew G. Messenger, 101 (1) The Society for Investigative Dermatology, Inc., pp. 4S–9S (Jul. 1993).

"Influence of Nonionic Liposomal Composition on Topical Delivery of Peptide Drugs into Pilosebaceous Units: An In Vivo Study Using the Hamster Ear Model," Pharmaceutical Research, vol. 12, No. 8(1995) Susan M. Neimiec, et al., pp 1184–1188.

Tushar Patel, et al., "The Role of Proteases During Apoptosis," Review, as cited in 10 Faseb J., pp 587–597 (1996).

Melanogenesis Is Coupled to Murine Anagen: Toward New Concepts for the Role of Melanocytes and the Regulation of Melanogenesis in Hair Growth, Andrzej Slominski et al., 101 (1) The Journal of Investigative Dermatology, Inc. pp. 90S–97S (Supp. Jul. 1993).

Stenn, et al., "Glucocorticoid Effect on Hair Growth Initiation: A Reconsideration," Skin Pharmacol 1993:6:125–134.

"Cytokine Expression on Keratinocytes in Alopecia Areata," Abstracts, Telegdy E. et al. 3 Exp. Dermatol. 147 (1994) Abstract).

Vaux, et al, "The Molecular Biology of Apoptosis," Proc. Natl. Acad. Sci, USA, vol. 93, pp. 2239–2244, Mar. 1996.

Characterization of Epidermal Cytokine Profiles in Sensitization and Elicitation Phases of Allergic Contact Dermatitis as Well as Irritant Contact Dermatitis in Mouse Skin Lymphokine and Cytokine Research, vol. 13, No. 6, (1994,) Kondo et al., pp. 367–375.

Lauer, et al. "Targeted Delivery to the Pilosebaceous Unit Via Liposomes," Advanced Drug Delivery Reviews, 18 (1996) 311–324.

Hoffmann, et al., Cytokines and Growth Factors Influence Hair Growth in vitro Possible Implications for the Pathogeneis and Treatment of Alopecia Areata, Arch. Dermatol. Res. 288:153–156 (1996).

"Cell Death in Health and Disease: The Biology and Regulation of Apoptosis," Christopher O. C. Bellamy, et al., Cancer Biology, vol. 6, (1995): pp 3–16.

"Tyrosinase: A Comprehensive Review of its Mechanism," Alvaro Sanchez–Ferrer, et al. Biochimica et Biophysica Acta 1247 (1995) 1–11.

"Distribution of Extracellular Matrix Molecules in Human Hair Follicles," A. G. Messenger, et al. 642 Acad. Sci. 253–262 (1991).

Panaretto et al., "Gene Expression of Potential Morphogens during Hair Follicle and Tooth Formation: A Review," Reprod. Fertil. Dev. 1993, 5, 345–60.

"Inflammatory Skin Disease in Transgenic Mice that Express High Levels of Interleukin 1–alpha in Basal Epidermis," Groves, et al. Proc. Natl. Acad. Sci. USA, vol. 92, pp. 11874–11878, Dec. 1995.

Cytokine mRNA Levels in Alopecia Areata Before and After Treatment with the Contact Allergen Diphenylcyclopropenone, Hoffmann, et al. 103 (4) The Journal of Investigative Dermatology, Inc. pp. 530–533 (Oct. 1994).

Gavrieli, et al., "Identification of Programmed Cell Death in situ via specific labelling of Nuclear DNA Fragmentation." 119 Jl. Cell Biology, 493–501 (1992).

Chomcymski, "Single Step Method of RNA Isolation By Acid Thiocyanate–phenol– chloroform extraction" 162 Anal. Biochem 156–159 (1987).

"RNAase free DNAase" protocol published by Promega, Corp. (1995).

"Superscript Reverse Transcriptase" protocol published by Life Technologies, Inc. (1990).

Shimizu P. Pommier Y,, Experimental Cell Research 2226(2):292:301, Aug. 1, 1996, Abstract: DNA. Fragmentation Induced by Protease Activation in p53—Null Human Leukemia HI 60 Cells Undergoing Apotosis Following Treatment with the Topoisomerase 1 Inhibitor Camptothein: Cell–Free System Studies.

Protopapa, et al., "Effects of Proteolytic Enzymes Papain, Chymotrypsin and Trypsin on the Guinea Pig Skin, with Special Reference to the Hair Follicle" *Epitheorese Klinikes Farmakologias Kai Farmakokinetikes, International Edition* 8 (1994) 84–88.

* cited by examiner

FIG. 1

Bar=10μm

Bar=10μm in (a-c)
Bar=5μm in (d)

FIG. 3B

Bar=10μm in (a-e)
Bar=5μm in (f)

```
                         SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

AACCCCAAGT TCCTGAAG                                                     18

(2) INFORMATION FOR SEQ ID NO:2:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

TTTGTGCTGG GCCACTTC                                                     18

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

TCAGCCCAGC ATCCTTCTTC                                                   20

(2) INFORMATION FOR SEQ ID NO:4:
```

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CAGCCATTGT TCAAAAATAC TGTCC                                              25

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AAAAGAAGAG AGAAGAGCGA C                                                  21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGAGCTGAGA CACCCTTACC                                                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAGACCCCAA CCCTAAGCAC                                                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAGCACTGAC GGTTTTCACC                                                    20
```

METHODS FOR ALTERING HAIR GROWTH AND HAIR PIGMENTATION BY APOPTOSIS IN THE FOLLICULAR PAPILLAE AND COMPOSITIONS THEREFOR

CROSS-REFERENCE TO RELATED APPLICATION

This Application claims the benefit of U.S. Provisional Application No. 60/021,629 filed on Jul. 12, 1996, which is incorporated by reference in its entirety.

FIELD OF THE INVENTION

This invention is related to methods for bringing about programmed cell death and apoptosis in the follicular papillae and compositions effective for the same. More specifically, the present invention is directed to methods for changing the rate of hair growth and hair pigmentation by topical application of either a protease or a molecule that affects a receptor-mediated signal transduction pathway.

BACKGROUND OF THE INVENTION

One main function of mammalian hair is to provide environmental protection. However, that function has largely been lost in humans, in whom hair is kept or removed essentially for cosmetic purposes.

Many procedures are used to remove unwanted hair including shaving, electrolysis, plucking and injection of therapeutic antiandrogens. These conventional methods are not without their shortcomings. Shaving, for instance, may result in nicks and cuts in the skin's surface, may leave a perception of an increase in the rate of hair regrowth, and may also leave an undesirable stubble. While electrolysis may keep an area free of unwanted hair for a prolonged period of time, the process is often expensive and painful and may further result in scarring. Not only may plucking cause pain and discomfort, but if often results in a poor removal of short hair. Several unwanted side effects, such as effects on muscularity, often accompany the use of antiandrogens. Furthermore, with the exception of electrolysis, all of these methods must be repeated on what is often a daily basis, creating an inconvenience for the user. For these reasons, chemical-methods for delaying hair growth are needed.

As disclosed in U.S. Pat. No. 5,455,234 by Ahluwalia, et al, mammalian hair growth may be altered by applying a cysteine pathway enzyme inhibitor to the skin, which will slow or stop the metabolic pathways for rate and character of hair growth with which cysteine is associated. However, this inhibition of cysteine also causes a shortage of this amino acid in the treated area. Similarly, in U.S. Pat. No. 5,095,007 by Ahluwalia, U.S. Pat. Nos. 5,096,911 and 5,468,476 by Ahluwalia et al. and U.S. Pat. Nos. 5,132,293 and 5,143,925,by Shander et al., enzyme inhibitors are utilized to alter hair growth. In each of these cases a biochemical pathway was altered to inhibit the production of a final product.

It would be desirable to provide a method for chemically affecting hair growth and hair pigmentation which does not deprive the user of needed amino acids or cause unwanted side effects to the user.

SUMMARY OF THE INVENTION

In accordance with the present invention, we have found a method for affecting changes in mammalian hair growth and hair pigmentation comprising, consisting essentially of, or consisting of:

topically applying to skin of a mammal an effective amount of a topically active composition comprising a protease within a time sufficient relative to telogen hair growth induction.

In another embodiment of the present invention, we have found a method for inducing programmed cell death and apoptosis within a follicular papilla comprising, consisting essentially of, or consisting of:

topically applying to skin of a mammal a topically active agent having a first portion which is similar in shape to a second portion of a three-dimensional structure of trypsin, whereby the first portion and the second portion are both capable of receptor-mediated signal transduction.

In another embodiment of the present invention, we have found a composition comprising, consisting essentially of, or consisting of:

a) a topically active agent having a first portion which is similar in shape to a second portion of a three-dimensional structure of trypsin, whereby the first portion and the second portion are both capable of receptor-mediated signal transduction; and b) a pharmaceutically or cosmetically acceptable vehicle.

In yet another embodiment of the present invention, we have found a composition comprising, consisting essentially of, or consisting of:

a) a topically active agent comprising a protease capable of inducing apoptosis in a follicular papilla; and b) a pharmaceutically or cosmetically acceptable vehicle.

The compositions and methods of this invention provide a unique, convenient means for delaying hair growth and hair pigmentation by inducing apoptosis at the follicular papillae.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The invention will be more fully understood and further advantages will become apparent when reference is made to the following detailed description of the invention and the accompanying drawings in which:

FIG. 2(a–c) are color representations of the dorsal view of the skin of C57BI/6 mice, some of which were treated with vehicle or trypsin (1%) immediately after induction for hair growth, taken: (a) 8 days after hair growth induction; (b) 11 days after hair growth induction; and (c) 14 days after hair growth induction. In FIG. 2(a), the left mouse was treated, while the right mouse was untreated. In FIGS. 2(b) and 2(c), the left mouse was untreated, the center mouse was treated with the vehicle and right mouse was treated with trypsin.

FIG. 5(a–b) is a representation which illustrates the profile of gene expression of a trypsin-treated mouse skin and an untreated mouse skin during a delayed hair cycle as detected by Reverse Transcription-Polymer Chain Reaction ("RT-PCR").

DETAILED DESCRIPTION OF THE INVENTION

As used herein, "mammal" shall mean any member "of the higher vertebrae animals comprising the class Mammalia," as defined in Webster's Medical Desk Dictionary 407 (1986), and includes but is not limited to humans. As used herein "(%, w/v)" shall mean grams of a given component per 100 ml of the total composition. As used herein, "receptor" shall include both intracellullar and extracellular receptors and shall mean those molecules capable of receiving and transducing a signal.

Topically active agents suitable for use in the composition of the present invention include proteases, compounds having a structure substantially similar to a portion of the three-dimensional structure of trypsin, or mixtures thereof.

Preferred proteases are the serine proteases which include, but are not limited to, trypsin, carboxypeptidase-Y, protease IV, subtilysin, or mixtures thereof. The protease of choice is trypsin. While not willing to be bound by this theory, we believe that the proteases capable of delaying hair growth and hair pigmentation do so by altering the hair growth cycle via the induction of programmed cell death and apoptosis within the follicular papillae, and that this alteration is likely induced by a receptor-mediated signal transduction. Preferably, the protease is present in an amount, based upon the total volume of the composition of the present invention, of from about 0% (w/v) to about 5% (w/v), and more preferably from about 0.01% (w/v) to about 1% (w/v).

As evidenced by Example 10 herein, we have unexpectedly found that the proteolytic activity of a protease is not the only factor which contributes to the induction of programmed cell death. While not wishing to be bound by any theory, we further believe that a receptor-mediated signal transduction event may also contribute to the induction of programmed cell death of the follicular papillae, and that this type of agent might be related to a structural component of the topically active agent.

Therefore, a second suitable topically active agent includes compounds which possess a portion that is substantially similar in shape to the portion(s) of a three-dimensional structure of a trypsin molecule that affect this receptor-mediated signal transduction. As used herein, "substantially similar in shape" means that the compounds include a sufficient amount of a structure behaving like a ligand which either may occupy a receptor, may displace a ligand from the receptor, or may activate or inactivate a receptor by a proteolytic cleavage, and thereby contribute to the induction of programmed cell death. Examples of such compounds possessing portions which are substantially similar in shape to the structure of a portion of three-dimensional trypsin include, but are not limited to proteolytically inactive trypsin, which is a form of trypsin that is unable to digest proteins such as collagen: Preferably these compounds are present in the composition of the present invention in an amount, based upon the total volume of the composition, of from about 0% (w/v) to about 5% (w/v) and most preferably from about 0.01% (w/v) to about 1% (w/v).

If the delivery parameters of the topically active pharmaceutical or cosmetic agent so require, the topically active composition of the present invention may preferably be further comprised of a pharmaceutically or cosmetically acceptable vehicle capable of functioning as a delivery system to enable the penetration of the topically active agent into the hair follicle. While any commercially available vehicle for delivering the protease to the appropriate skin appendage, which in this case is the hair follicle, is suitable for use as the pharmaceutically or cosmetically acceptable vehicle, liposomes are preferred. The liposomes are more preferably non-ionic and comprised of a) glycerol dilaurate or glycerol distearate; b) compounds having the steroid backbone found in cholesterol; and c) fatty acid ethers having from about 12 to about 18 carbon atoms, wherein the constituent compounds of the liposomes are in a ratio of about 53:10:22 to about 63:20:32, and preferably from about 55:12:24 to about 61:18:30, respectively. Liposomes comprised of glycerol dilaurate/cholesterol/polyoxyethylene-10-stearyl ether (GDL) are most preferred. Preferably the liposomes are present in an amount, based upon the total volume of the composition, of from about 10 mg/mL to about 100 mg/mL, and more preferably from about 25 mg/mL to about 50 mg/mL. A ratio of about 58:15:27 is most preferred. Suitable liposomes may preferably be prepared in accordance with the protocol set forth in Example 2, though other methods commonly used in the art are also acceptable.

The above described composition may be prepared by combining the desired components in a suitable container and mixing-them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 1184–88 (1995) ("Niemiec"), which is incorporated by reference herein in its entirety.

In a preferred embodiment, the pH of the topically active pharmaceutical or cosmetic composition may be adjusted with a known pH adjuster including but not limited to N-2-hydroxyethylpiperazine-N'-2-ethane sulfonic acid available from, for example, Life Technologies under the tradename "Hepes", or (hydroxymethyl)aminomethane, available from, for example, Life Technologies under the tradename, "Tris", citric acid, and mixtures thereof to yield a pH of from about 2 to about 8 in the final composition.

In alternative embodiments, the topically active pharmaceutical or cosmetic composition may be optionally combined with other ingredients such as moisturizers, foaming agents, cosmetic adjuvants, anti-oxidants, surfactants, foaming agents, conditioners, humectants, fragrances, viscosifiers, buffering agents, preservatives, and the like in an amount which will not destroy the liposomal structure in order to produce cosmetic or pharmaceutical products such as, non-exclusively, shaving creams, shaving gels, shaving powders, chemical depilatory creams and the like.

In another embodiment of the present invention, we have found a process for affecting changes in mammalian hair growth and hair pigmentation comprised of applying the topically active pharmaceutical or cosmetic composition to the surface of an animal's skin at about the time of hair growth induction.

Hair growth induction from telogen follicles can be performed by any method well-known in the art, including, but not limited to, shaving, wax depilation, chemical depilation and combinations thereof.

Although the time at which the topically active pharmaceutical or cosmetic composition is applied to the skin as well as the amount of time for which the composition remains on the skin may vary, one skilled in the art would readily realize without undue experimentation that the topically active composition is preferably applied to the skin surface either immediately before, immediately after or simultaneously with hair growth induction from a telogen state. As used herein, "immediately" shall be defined as within a period of about one hour. More preferably, the topically active pharmaceutical or cosmetic composition is applied either simultaneously with or immediately following hair growth induction and is left on the skin for a period sufficient to delay hair growth, which is preferably at least about five minutes and more preferably is at least about fifteen minutes after the time of application.

The topically active pharmaceutical or cosmetic composition should be applied in an amount effective to affect changes in mammalian hair growth and hair pigmentation. As used herein "amount effective" shall mean an amount sufficient to cover the region of skin surface where a delay in hair growth and hair pigmentation is desired. Preferably, the composition is applied to the skin surface such that, based upon a square cm of skin surface, from about 2 $\mu$l/cm$^2$ to about 8 $\mu$l/cm$^2$ of topically active agent is present when a delay in hair growth and hair pigmentation is desired.

We have unexpectedly found that when topically active agents, such serine proteases, are topically applied to an animal's skin at about the time of hair growth induction, a significant delay in hair growth and hair pigmentation of at least about 9 days was achieved. We further believe that since the hair growth cycle for humans is often slower than that for mice, it is further likely that the hair growth delay in humans would be considerably longer than 9 days.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Depilation of Test Subjects in the Mouse System

The hair growth of 12 C57BI/6 female mice obtained from Charles River (Kingston, N.Y.), which were 6–10 weeks of age and were in the resting (telogen) phase of their respective hair cycle, was induced by wax depilation (plucking) of each respective animal's back fur according to the procedure set forth in Stenn, et al., "Glucocorticoid Effect on Hair Growth Initiation: A Reconsideration," 6 Skin Pharmacol., 125–134 (1993). As well-known in mice, the growth phase (anagen) starts synchronously in all hair follicles at the time of depilation.

As illustrated in Table 1, the following observations were noticed at the induction site:

TABLE 1

Observations at Induction Site

| Days Post-Induction | MORPHOLOGICAL AND Histological Observations at the induction site |
| --- | --- |
| 1–2 (early anagen) | new follicle starts to grow |
| 3 to 4 | hair follicles were fully developed, but the hair shafts were not yet visible |
| 8 (late anagen) | each mouse had very dark skin; their hair shafts are histologically visible |
| 11–12 | the hair shafts started to penetrate through the epidermis. |
| 14 | each mouse was covered with short hairs |
| 19 | the regression of the follicle (catagen) was observed histologically |
| 21 to 25 | the hair follicle is back to resting phase. |

As shown in Table 1, the hair growth was visible several days after depilation as the pink skin of the animal began to darken. This is likely due to hair pigmentation in the shaft since the C57BI/6 mouse contained melanocytes only in the hair follicles and not in the epidermis.

The hair growth from telogen of 12 similar C57BI/6 mice was also induced by chemical depilation with a hair remover available from Carter-Wallace, Incorporated under the tradename "Nair" in an amount sufficient to wet the back of each mouse. In chemical depilation, the lower portion of the follicles remained intact and lower portions of hair shafts of the previous cycle remained intact in the dermis until pushed out by the newly-grown hairs. The growth pattern of the new hair cycle was identical to the one described in Table 1.

Figure 3A:
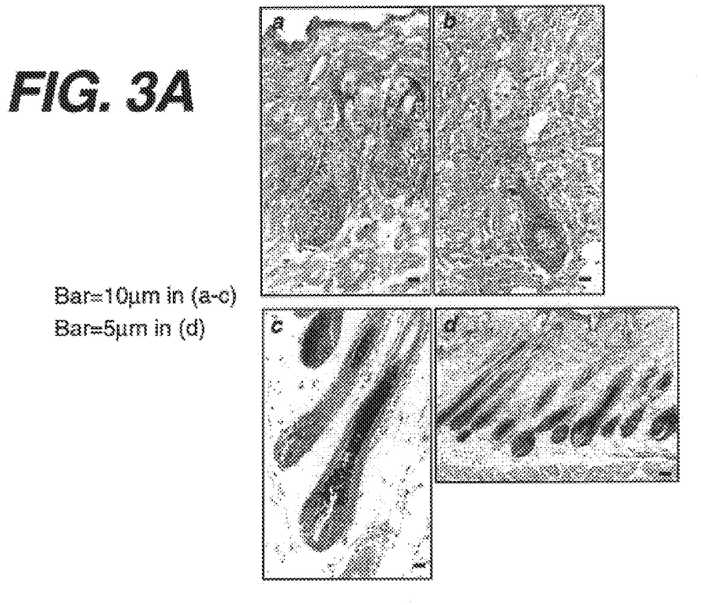
FIG. 3A is a representation which illustrates the histology of hair follicles of untreated mouse skins at: (a) 4 days; (b) 5 days; (c) 8 days; and (d) 12 days post hair induction.

Since the murine hair cycle varies not only between strains, but also amongst individual animals, a 2 cm by 1 cm skin sample was isolated from each mouse with scissors, fixed with a 10% buffered formalin solution having a pH of about 6.9–7.1 at 25° C. available from Stephens Scientific, and then formed into a paraffin block according to well-known procedures. The block was then microtomed, stained with H&E stain, and examined histologically in order to verify the phase of the hair cycle using procedures well-known in the art. The histological representations obtained from this Example are illustrated in FIG. 3A.

This Example shows that the hair growth cycle for C57BI/6 mice averaged about 25 days and reports similar timing of hair follicle and shaft development regardless of the method used for depilation.

Example 2

Preparation of Topically Active Compositions

A sufficient amount of lyophilyzed trypsin available from Sigma-Aldrich Corporation was mixed into a buffered aqueous solution of 0.05 M N-2-hydroxyethylpiperazine-N'-2-ethane sulfonic acid available from Life Technologies under the tradename "Hepes" such that the pH of the resulting solution was about 7.4 and the concentration of trypsin in the solution was about 2% (w/v). 1 volume of the resulting trypsin solution was then mixed with 1 volume of (5%) glycerol dilaurate/cholesterol/polyoxyethylene-10-stearyl ether liposomes in water vehicle, which was prepared by the methods described in Niemiec, in order to yield a 1% (w/v) concentration of trypsin in the resulting topically active composition.

Example 3

Delivery of Trypsin into Hair Follicles

Twelve days after plucking the hairs from about a 6 cm by 2 cm section of the skin surface of 4 C57BI/6 female, 7 to 8 week old mice available from Charles River (Kingston, N.Y.), about 100 μL/mouse of the topically active composition of Example 2 was applied thereto. The trypsin used in this Example was fluorescently-labeled with a FluoReporter protein labelling kit available from Molecular Probes, Inc. in accordance with its accompanying protocol (1997) and using a fluoroscein isothiocyanate (FITC) fluorescent label, also available from Molecular Probes, Inc.

At one and four hours after the application of the fluorescent trypsin treatment, a 2 cm×1 cm sample of the skin surface of each mouse was isolated and formed into a paraffin block which was then microtomed and examined histologically in accordance with the procedure set forth in Example 1.

Figure 1:
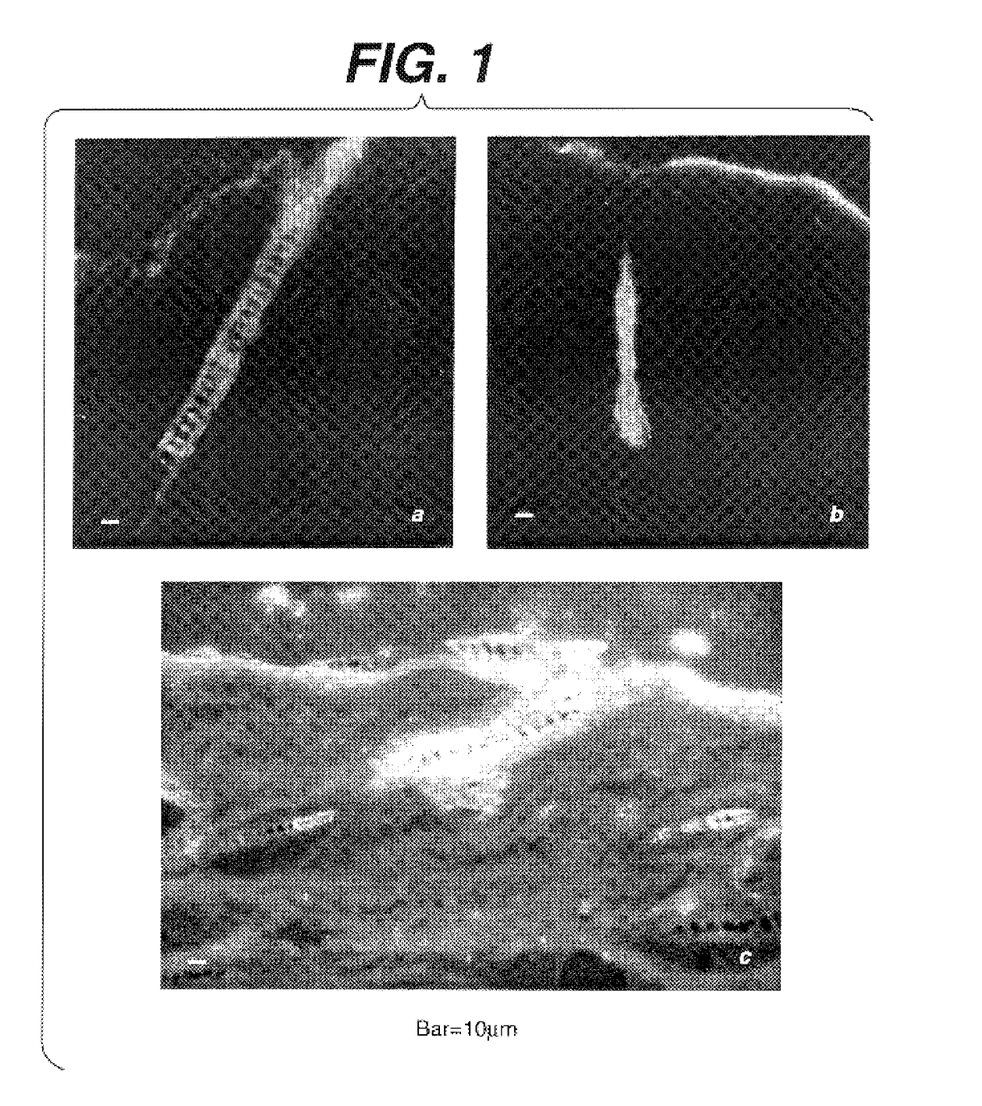
FIGS. 1(a) and 1(c) are representations which illustrate a cross-sectional view of the skin of an untreated C57BI/6 mouse-labeled with fluorescent trypsin.
FIG. 1(b) is a representation which illustrates a cross-sectional view of the skin of a C57BI/6 mouse 12 days post-topical treatment with trypsin mouse labeled with fluorescent trypsin.

As shown in FIG. 1, almost all of the fluorescent labeling was found within the hair follicle. The mice were examined at the 1 hour (FIG. 1(c)) interval and the 4 hour (FIG. 1(a)) interval displayed identical histological staining patterns, with no additional skin penetration at the later time point. This observation suggests against a possible non-specific extracellular matrix digestion by the protease, which would have likely shown a deeper penetration of the fluorescent stain into the stratum corneum at the later time point.

This Example was repeated on 4 similar C57Bl/6 female, 7 to 8 week old mice, but with the exception that the mice were also treated daily for 12 days post-induction with the 1% (w/v) trypsin treatment of Example 2. Four hours after the application of the fluorescent-trypsin treatment on the twelfth day post-induction, the skins of the mice were analyzed using similar histological methods. As illustrated in FIG. 1b, no major change was observed in the delivery route of the trypsin into the hair follicles of the treated skins. However, the minimal staining at the outer portion of the stratum corneum of the trypsin-treated skins indicated some loss of barrier integrity.

This Example shows that the application of a topically active composition containing trypsin to the skin surface of anagen animals resulted in the delivery of the trypsin primarily to the hair follicle, both after short term and long term use.

Example 4

Trypsin Delays Hair Growth and Hair Pigmentation

A single topical application of the topically active composition prepared in Example 2 was applied to 12 C57Bl/6 female, 7 to 8 week old mice immediately after hair growth induction in accordance with the method set forth in Example 3.

Figure 2A:
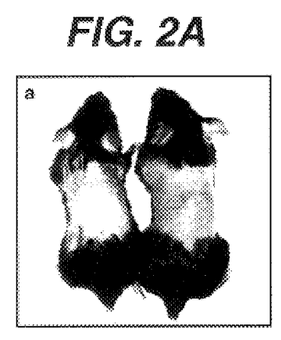
Figure 2B:
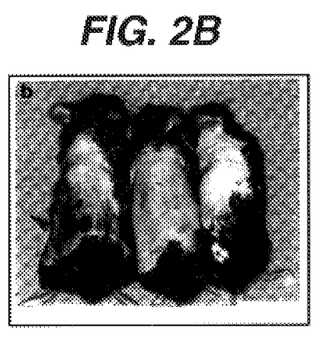
Figure 2C:
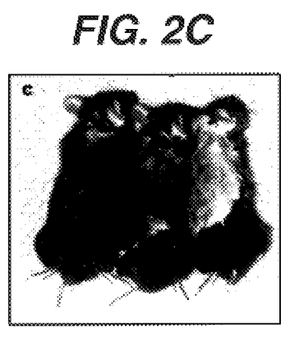

As shown in FIG. 2, a single application of trypsin applied post-hair growth induction delayed both hair growth and hair pigmentation. The darker skin color indicated a more progressive stage of the hair cycle, which is before the hair shafts were visible. Untreated and liposome (vehicle)-treated controls exhibited dark skin at 7–8 days post-hair growth induction (FIG. 2a; left is treated and right is untreated), while their hair shafts were visible at 11–13 days (FIG. 2b; left is untreated; middle is vehicle; right is treated). By contrast, the trypsin-treated animals remained pink until day 8 (FIG. 2a; left mouse); were slightly darker pink at day 11 (FIG. 2b; right mouse); and exhibited gray skin by day 14 (FIG. 2c; right mouse). Although the hair shafts of the trypsin-treated animals were first visible at days 15 to 17, these hair shafts were of reduced quality and were not as thick as in the control; however, within about 4 to 7 additional days, these hair shafts were almost indistinguishable from those in the controls in all characteristics except for length.

This Example shows that trypsin was effective for delaying both hair growth and hair pigmentation.

Example 5

Histology of Trypsin Treated Hair Follicles

A single topically active composition as prepared in Example 2 was applied to the skin surface of 3 C57BL/6 female, 7 to 8 week old mice after hair induction in accordance with the method set forth in Example 3.

Figure 3B:
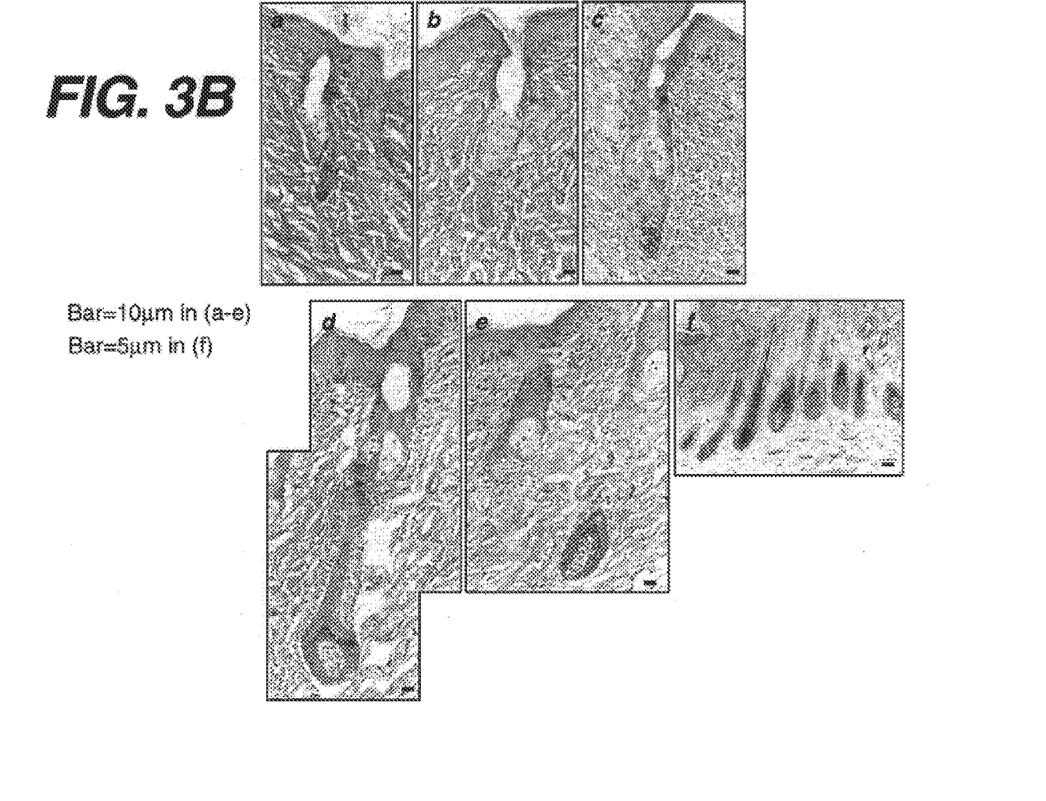
FIG. 3B is a representation which illustrates the histology of hair follicles of trypsin-treated mouse skins at: (a) 4 days; (b) 5 days; (c) 6 days; (d,e) 8; and (f) 12 days post hair induction.

1 cm×2 cm samples of the skins of untreated, vehicle-treated (not shown), and trypsin-treated mice were obtained, H&E stained, then examined histologically via the procedure set forth in Example 1. As illustrated in FIG. 3, histological analysis of the stained samples evidenced that the development of the hair follicles in trypsin-treated mice was significantly delayed. More specifically, the characteristic layered structure, the expanded follicular papillae and the new hair pigmentation were first observed several days later than the date of first observation of such characteristics in the untreated and vehicle-treated controls. In addition, the follicles in the skin of trypsin-treated mice displayed a dilated infundibulum, as best illustrated in FIG. 3B(a–e), which was not present in the untreated and the vehicle-treated mice as shown in FIG. 3A(a–b). This observation supports the fact that treatment with the trypsin-containing composition also resulted in hair growth having a reduced quality, i.e. thinner and more sparse. At 7–8 days post-treatment with trypsin, the lower part of some treated follicles started to form an epithelial layering structure as illustrated in FIG. 3B(d–e), but the upper part still displayed an empty structure as best shown in FIG. 3B(d). By 11–12 days post-treatment with trypsin, most of the treated follicles matured, but still displayed reduced hair pigmentation and shorter shaft length that resembled the characteristics of the untreated follicle at 4 to 5 days post-induction (compare FIG. 3A(d) to FIG. 3B(f)).

This Example further showed via histological analysis that the topical application of trypsin to the skin of hair growth induced mice significantly delayed hair growth and hair pigmentation.

Example 6

Trypsin Induces Apoptosis at the Follicular Papillae

A single topically active composition as prepared in Example 2 was applied to the skin surface of 3 C57BL/6 female, 7 to 8 week old mice after hair induction in accordance with the method set forth in Example 3.

1 cm×2 cm samples of the skins of untreated and trypsin-treated mice were obtained via the procedure set forth in Example 1 then analyzed via a TdT-mediated dUTP-biotin nick end labeling ("TUNEL") procedure as disclosed in Gavrieli et al., "Identification of Programmed Cell Death in situ Via Specific Labelling of Nuclear DNA Fragmentation", 119 Jl. Cell Biology 493–501 (1992)("Gavrieli"). During this procedure, the prepared paraffin sections of the skins were stained using an "ApopTag™ Plus InSitu Apoptosis Detection Kit" available from Oncor, Inc. as specified in the "ApopTag™ Plus InSitu Apoptosis Detection Kit" protocol by Oncor, Inc. (February 1995), which is based upon the labeling of fragmented DNA ends as described in Gavrieli. FIG. 4 shows a histological analysis wherein the stain has a peroxidase end point (brown) and a methyl green counter-stain.

Similarly, paraffin sections suitable for TUNEL staining were prepared from the untreated skins of mice. These sections were stained and analyzed histologically; the resulting representations of which are provided in FIG. 4A(a–c).

Figure 4A:
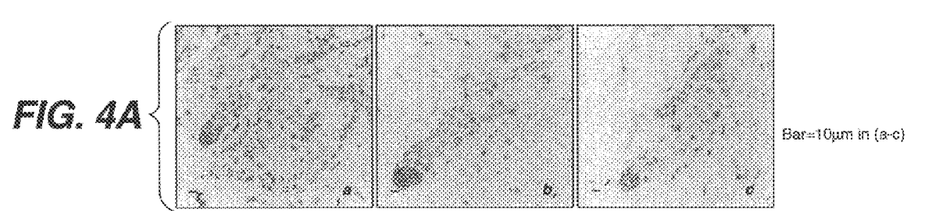
FIG. 4(A) is a representation which illustrates the cross-sectional view of TUNEL-stained skin tissue of an untreated mouse at: (a) 1 day; (b) 2 days; and (c) 3 days post hair induction.
Figure 4B:
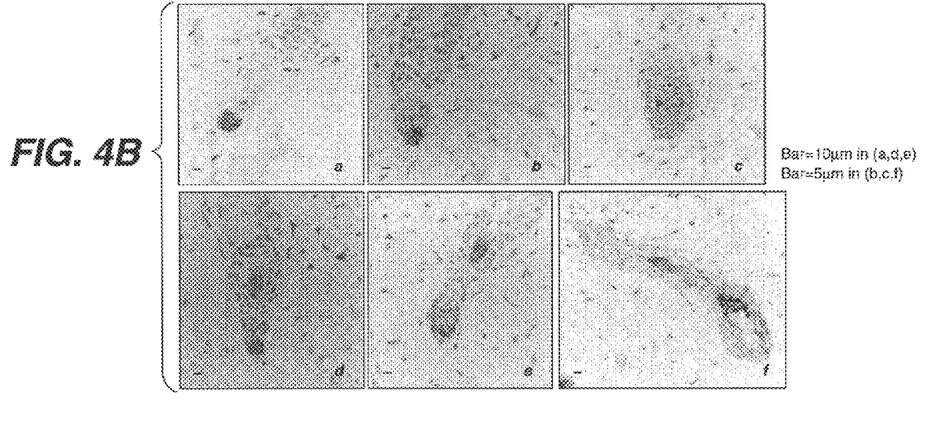
FIG. 4(B) is a representation which illustrates the cross-sectional view of TUNEL-stained skin tissue of a trypsin-treated mouse at: (a) 1 day; (b) 2 days; (c) 3 days; (d) 4 days; (e) 5 days post hair induction ((a–e) were single trypsin applications); and (f) 8 days post hair induction (daily trypsin applications).

As illustrated in FIG. 4, the TUNEL-stained samples defined apoptotic cells by both morphology (condensed or fragmented nuclei and cytoplasm or apoptotic bodies) and by the color of its stain (fragmented DNA within the condensed nuclei were stained brown). More specifically, FIG. 4B(a–e) illustrated that apoptotic bodies were detected within the treated follicular papilla throughout the first week after hair growth induction. However, no other portions of the follicle, epidermis or dermis were affected by the trypsin treatment. By contrast, a minimal level of apoptosis was occasionally detected in untreated early anagen follicles as illustrated in the TUNEL-stained untreated sample in FIG. 4A(a–c); however, the apoptosis was always at the isthmus of the follicle and thus well above the follicular papilla. Most of the untreated follicles did not display any cell death.

This Example showed that the application of trypsin to depilated skin resulted in an increase in apoptotic figures within the follicular papillae of the trypsin treated follicles, relative to that of either untreated or vehicle treated controls.

Example 7

Trypsin Induces Changes in Gene Expression During the Hair Cycle

A single topically active composition as prepared in Example 2 was applied to the skin surface of 6 C57BL/6 female, 7 to 8 week old mice after hair induction in accordance with the method set forth in Example 3.

At the time intervals indicated in FIG. 5, the skins of untreated mice and trypsin-treated mice were obtained as described in Example 1, then their total RNAs were extracted using "RNA Stat-60" reagent available from Tel-Test "B," Incorporated as described in Chomczymski, "Single Step Method of RNA Isolation By Acid Guanidinium Thiocyanate-phenol-chloroform extraction," 162 Anal. Biochem. 156–59 (1987). A sufficient amount of RNase-free DNase available from Promega, Corporation under the tradename "RQ1RNase-free DNase" was then added to the extracted RNA from each mouse such that each respective product contained 200 ng of DNased-RNA using the procedure set forth in "RNase-free DNase", protocol published by Promega, Corporation (May, 1995). The resulting 200 ng of DNased-RNA was reverse transcribed ("RT") via the procedure set forth in "Superscript II Reverse Transcriptase" a protocol published by Gibco-BRL (now Life Technologies, Incorporated) (April 1992), using random hexamers such as the random primers which are commercially available from Life Technologies, Incorporated.

The resulting RT products were then amplified via polymerase chain reaction ("PCR") using about a 0.5 unit (per 100 $\mu$l reaction) of a thermostable DNA polymerase which is commercially available from Perkin-Elmer-Cetus Corporation under the tradename "Taq polymerase" and about 0.1 $\mu$mol/reaction of gene-specific primers available from Clontech Laboratories, Inc. ("Clontech") or designed as set forth in Table 2 in accordance with the procedures set forth in the protocol accompanying the primers from Clontech for mouse glyceraldehyde-3-phosphate-dehydrogenase (G3PDH), transcription factors and cytokines, or as described in Table 2.

Table 2 illustrates some of the DNA primers used, the amount of $MgCl_2$ required for the PCR reaction, and the length of the PCR cycle.

TABLE 2

DNA Primers Utilized in RT-PCR Assay***

| Primer (See attached Sequence Listing) | Amt. of $MgCl_2$ (mM) | Cycle (min) @ ° C. | No. of cycles | DNA Seq. ID No. |
|---|---|---|---|---|
| Transglutaminase sense AACCCCAAGT TCCTGAAG | 2.5 | 1 @ 94; 2 @ 55; 3 @ 72 | 35 | 1 |
| Transglutaminase antisense TTTGTGCTGG GCCACTTC | 2.5 | 1 @ 94; 2 @ 45; 3 @ 72 | 35 | 2 |
| Tyrosinase sense TCAGCCCAGC ATCCTTCTTC | 5 | 1 @ 94; 2 @ 45; 3 @ 72 | 35 | 3 |
| Tyrosinase antisense CAGCCATTGT TCAAAAATAC TGTCC | 5 | 1 @ 94; 2 @ 55; 3 @ 72 | 35 | 4 |
| Proopiomelanocortin ("POMC") sense AAAAGAAGAG AGAAGAGCGA C | 2.5 | 1 @ 94; 2 @ 55; 3 @ 72 | 35 | 5 |
| POMC antisense AGAGCTGAGA CACCCTTACC | 2.5 | 1 @ 94; 2 @ 55; 3 @ 72; | 35 | 6 |
| Collagenase sense AAGACCCCAA CCCTAAGCAC | 2.5 | 1 @ 94; 2 @ 53; 3 @ 72 | 35 | 7 |
| Collagenase antisense CAGCACTGAC GGTTTTCACC | 2.5 | 1 @ 94; 2 @ 53; 3 @ 72 | 35 | 8 |

The PCR products were then analyzed by 2% agarose/ethidium bromide gels and analyzed according to methods well-known in the art in order to compare the level of expression of certain genes during the hair cycle of both trypsin-treated and untreated mice. When necessary for better visualization, the resulting PCR products were precipitated with ethanol according to well-known procedures. When primers for G3PDH were used, only 10% of the PCR reaction products were used. An RNA sample from the skin of a C57BL/6 female, 7 to 8 week old mouse that was not reverse-transcribed was used as a negative control for each PCR amplification. An RNA sample from the skin of a six month old C57BI/6 female mouse having a non-synchronized hair cycle was used as a positive control when positive controls were not commercially available. The migration of the RT-PCR products on the gels was always identical to that of the positive controls, and to that of the reported amplimer sizes.

The relative quality of each respective RT-PCR reaction product was then compared by analyzing the mRNA level of G3PDH, a "housekeeping" gene, in each respective product. As illustrated in FIG. 5, G3PDH gene expression was found to be similar at all the time points examined, which thereby enabled the comparison of the relative levels of gene expression for the desired genes.

To verify that the delay in follicular development was not the result of a non-specific irritation or inflammatory response, we analyzed the mRNA levels of genes that are typically upregulated during such situations. After examination of the mRNA levels of genes from the RT-PCR products, we found that there was no change in the mRNA levels of IL-6, IL-10 and GM-CSF, a slight upregulation of TNF$\alpha$, a slight down regulation of TNF$\beta$ and TNF-RI, and a moderate down regulation in Macrophage Inducible Protein (MIP) as illustrated in Table 3.

TABLE 3

Patterns of Gene Expression

| Gene | Untreated | Trypsin-Treated |
|---|---|---|
| IL-6 | − | − |
| IL-10 | +/− | +/− |
| GM-CSF | − | − |
| TNFα | +/− | + |
| TNFβ | + | +/− |
| TNF-RI | +/− | +/− − |
| TNF-RII | − | − |
| MIP | + | − |
| IL-1α | + | ++ |
| IL-1β | +/− | +++ |
| IL-1R | − | − |
| IFNγ | − | +++ |
| c-myc | + | − |
| c-myb | ++ | + |
| c-fos | + | +/− |
| c-jun | +/− | + |
| Collagenase | + | +/− |
| Tyrosinase | +++ | +/− |
| POMC | + | +/− |
| Transglutaminase | + | + |

*Note that RT-PCR is only semi-quantitative. Comparisons are valid only for each amplified sequence within the different hair cycles, and not among the different genes.
− no detectable expression
+/− − a very weak band
+/− a weak band
+ a strong band
++ a stronger band
+++ a very strong band The profile of gene expression in Table 3 suggests against an inflammatory reaction or a response to dermal irritation.

A moderate upregulation was observed in IL-1α mRNA level (FIG. 5b & Table 3), a gene associated with the inhibition of hair growth in culture. Since the 1L-1α induction could have also resulted from the loss of the epidermal barrier function, we analyzed the barrier integrity by measuring transepidermal water loss (TEWL). TEWL was measured with an "Evaporimeter EPI" evaporimeter available from Servomed AB by first normalizing the evaporimeter with the ambient humidity and then placing the probe on the dorsal skin of the test subject. The results showed only a moderate increase in TEWL which did not correlate with trypsin concentration as shown in Table 4.

TABLE 4

TEWL in Trypsin Treated Skins

| Treatment | Sample Size | TEWL |
|---|---|---|
| Untreated | 6 | 27.01 ± 3.8 |
| 0.01% Trypsin | 4 | 36.89 ± 4.6 |
| 0.1% Trypsin | 4 | 43.2 ± 5.2 |
| 0.5% Trypsin | 4 | 34.53 ± 4.9 |
| 1% Trypsin | 4 | 37.5 ± 3.9 |
| 1% Trypsin - inactive (mild) | 3 | 33.99 ± 6.2 |

Therefore, it is likely that any upregulation of IL-1α in our RT-PCR product as illustrated in Table 3 and FIG. 5 is associated with the inhibition of hair growth.

Figure 5A:
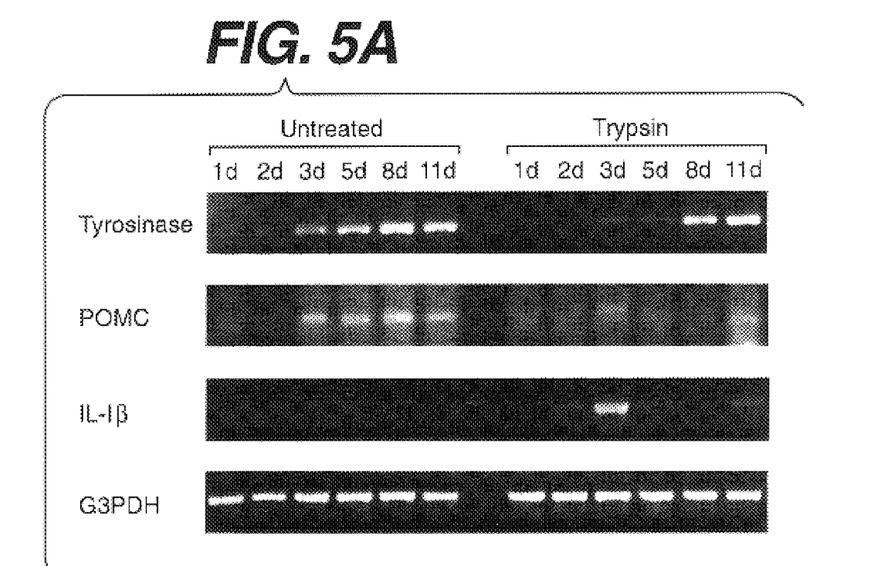
FIG. 5(A) illustrates the mRNA levels throughout days 1 to 11 of the delayed hair cycle.
Figure 5B:
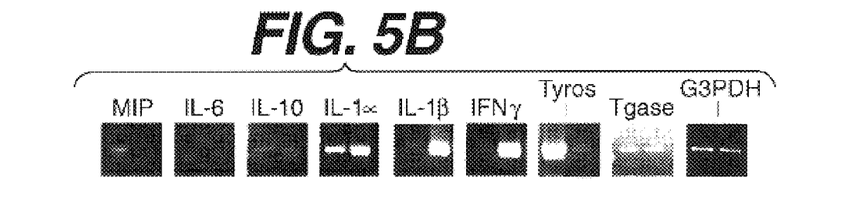
FIG. 5(B) illustrates the mRNA levels at day 8 of the delayed hair growth cycle. The RT-PCR products of 25 ng (A) and 250 ng (B) of total RNA are shown.

As illustrated in FIGS. 5a–b & Table 3, a stronger increase in mRNA levels was demonstrated for 1L-1β and IFNγ, which Are both known to be upregulated in Alopecia Areata and to be associated with the inhibition of hair growth. This further suggested that the only inflammatory-associated genes upregulated by trypsin were those associated with inhibition of hair growth.

As illustrated in Table 3, a slight reduction was detected in the mRNA levels of c-myb, c-myc and c-fos, while c-jun level was slightly increased throughout the delay period. Collagenase, a gene regulated via an AP-1 response element, was slightly reduced as well. This observation of a general slight reduction in mRNA levels of several genes was further reflective of the overall slow down in hair growth of trypsin-treated skin.

As illustrated in FIG. 5A and Table 3, tyrosinase, a key enzyme for hair pigmentation, was downregulated during the delay in hair growth period, while its mRNA level increased as the follicles started to overcome the delay. POMC, the precursor of the melanogenic peptide melanocyte stimulating hormone (MSH), was moderately downregulated throughout the delay period as shown in FIG. 5A and Table 3. The downregulation of these two genes indicated that trypsin also affected the regulation of hair pigmentation.

This Example showed that the trypsin perturbation of the hair cycle may be understood by examination of the expression pattern of a series of genes throughout the delay period. Trypsin-induced changes in mRNA levels along the hair-cycle were clearly evidenced, indicating a regulatory role for trypsin in hair growth and hair pigmentation. Moreover, this Example further reflected the specificity of the topical application of trypsin on hair growth and hair pigmentation genes.

Example 8

Other Serine Proteases Which Affect Hair Growth

A single topically active composition as prepared in Example 2 was applied to the skin surface of C57BL/6 female, 7 to 8 week old mice after hair induction in accordance with the method set forth in Example 3.

The procedure of Example 3 was repeated, but with the substitution of carboxypeptidase-Y, protease IV, and subtilysin, respectively, for the trypsin.

After 8 days post-treatment, the skin of each respective mouse was examined using a Minolta Chromameter Model CR300 chromameter in order to compare their respective skin colors.

We observed that trypsin, a member of the endopeptidase family which cuts a protein at the C-side of Arginine and Lysine, induced the longest delay in hair growth. By contrast, the carboxypeptidase-Y, which hydrolyzes L-amino acids at the C-termini of proteins, and protease IV, a member of the nonspecific endopeptidase family which cuts 56% of peptide bonds at neutral pH, had only minimal delaying effect, while subtilysin, a member of the nonspecific peptidase family which cuts peptide bonds at alkaline pH, only slightly increased the rate of hair growth. The results of this Example are illustrated in Table 5.

TABLE 5

Color Measurements of Serine Protease Treated Skins

| Treatment | Sample Size | L* |
|---|---|---|
| Untreated | 6 | 49 ± 0.30 |
| 1% Trypsin | 6 | 56.1 ± 0.81 |
| 1% Subtilysin | 4 | 42.9 ± 2.87 |
| 1% Endopeptidase | 4 | 51.8 ± 0.11 |
| 1% Carboxypeptidase-Y | 4 | 51.9 ± 0.47 |

(The L* scale: 0 = black and 100 = white, is a measure of hair pigmentation as viewed from the skin surface.)

As illustrated in Table 5, the trypsin-treated hair follicles were the least developed and thus appeared to impart the lightest color to the skin. This Example suggests that the appearance of skin color is related to hair development in the hair follicle.

Since the results obtained from the trypsin-treated skins showed trypsin to be relatively superior at delaying hair growth and hair pigmentation, this Example supports the belief that the effect of trypsin on hair growth and hair pigmentation may not be exclusively the result of a non-specific proteolytic digestion, but rather it may also be the result of a specific activity induced by trypsin that causes the activation of the programmed cell death pathway.

Example 9

Trypsin Affects an Early Step in Hair Growth Induction

A single topically active composition as prepared in Example 2 was applied to the skin surface of 3 C57BL/6 female, 7 to 8 week old mice after hair induction in accordance with the method set forth in Example 3. This procedure was repeated on nine additional mice, but the treatment was applied either two, three or seven times per week, respectively.

After observing the skin color of the mice for 8 days, the skin of the treated mice was lighter than that for the untreated controls. This further suggested that the trypsin-treated hair follicles were the least developed and thus appeared to impart the lightest color to the skin.

1 cm×2 cm samples of the skins of the respectively-treated mice were obtained, H&E stained, then examined histologically via the procedure set forth in Example 1. Histological analysis of the stained samples supports the fact that the additional daily treatments of the animals with trypsin did not prolong the delay in hair growth. This indicated that the induction of cell death by a serine protease resulted from a specific and timely event.

In order to determine the timing of this specific event, a single topically active composition as described in Example 2 was applied to the skin surface of C57BL/6 female, 7 to 8 week old mice after hair induction in accordance with the method set forth in Example 3, except that the treatment was applied at various time intervals as indicated in Table 6.

As illustrated in Table 6, the skin color chromametric measurements obtained in accordance with the method set forth in Example 8 demonstrated an increase in darkness (more pigment, less of the delay) that correlated with the increased time between hair growth induction and trypsin application. Mice treated immediately after hair growth induction showed the longest delay in hair growth and hair pigmentation. Mice treated 2 hours and 4 hours after hair growth induction also exhibited a delayed, but progressively shorter hair cycle. Mice treated 6 or more hours after depilation were not delayed for hair growth and were indistinguishable from the untreated control.

TABLE 6

Color Measurements of Trypsin Treated Skin**

| Treatment | Sample Size | L* |
| --- | --- | --- |
| Untreated | 6 | 49 ± 0.32 |
| 1% Trypsin, immediately | 6 | 56.1 ± 1.54 |
| 1% Trypsin, after 2 hours | 4 | 54.4 ± 1.30 |
| 1% Trypsin, after 4 hours | 4 | 53.3 ± 1.23 |
| 1% Trypsin, after 6 hours | 4 | 48.0 ± 2.01 |

TABLE 6-continued

Color Measurements of Trypsin Treated Skin**

| Treatment | Sample Size | L* |
| --- | --- | --- |
| 1% Trypsin, after 18 hours | 4 | 49.2 ± 1.07 |
| 1% Trypsin, after 48 hours | 4 | 50.4 ± 1.01 |

**Skin samples were tested 8 days post-depilation.

This Example shows that the application of trypsin to the skin is effective for delaying hair growth and hair pigmentation when applied within about 4 hours, and preferably immediately after hair growth induction.

Example 10

The Trypsin Effect May Involve a Receptor-Mediated Pathway

A single topically active composition as prepared in Example 2 was applied to the skin surface of C57BL/6 female, 7 to 8 week old mice after hair induction in accordance with the method set forth in Example 3, with the exception that the concentration of the trypsin was varied between 1% (w/v) to 0.01% (w/v) ($4 \times 10^{-4}$ M–$4 \times 10^{-6}$ M). At 9 days post-depilation, the mice were analyzed calorimetrically via the procedure set forth in Example 9.

As illustrated in Table 7, the results of the calorimetric analysis showed an increase in brightness (L*, more white, less pigment) which correlated with a decrease in trypsin concentration and with an increase in the delay of the hair cycle.

TABLE 7

Skin Brightness of Trypsin Treated Skins**

| Treatment | Sample Size | L* |
| --- | --- | --- |
| Untreated | 6 | 45 ± 0.97 |
| 0.01% Trypsin | 4 | 48.6 ± 1.01 |
| 0.1% Trypsin | 4 | 49.5 ± 1.07 |
| 0.5% Trypsin | 4 | 47.7 ± 0.3 |
| 1% Trypsin | 4 | 47.9 ± 0.08 |
| 1% Trypsin-inactive (mild) | 3 | 52.2 ± 0.17 |

*L scale: 0 = black, 100 = white
**Samples were analyzed 9 days post-depilation.

Example 11

The Proteolytic Activity of Trypsin is Unnecessary for Delaying Hair Growth

After the composition of Example 2 was incubated at room temperature for 48 hours, its proteolytic activity was analyzed via a serine protease activity detection kit available from PanVera, Corporation, which showed that the preparation had no detectable proteolytic activity. The inactive composition was applied to the skin surface of 3 C57BL/6 female, 7 to 8 week old mice after hair induction in accordance with the method set forth in Example 10. At 9 days post-depiliation, the mice were analyzed colorimetrically via the procedure set forth in Example 8. As illustrated in Table 7, it was evident that the lack of proteolytic activity of trypsin did not reduce the activity of this preparation in delaying hair growth.

This Example was repeated, except that the incubated trypsin was substituted with trypsin boiled for 10 minutes at temperature of 100° C. The results showed that the use of boiled trypsin, which was proteolytically inactive as well, had no delaying effect on hair growth. The act of boiling, which denatured the three-dimensional structure of trypsin, suggested that the three-dimensional structure of trypsin, and not just its proteolytic activity, contributed to the delaying effect on the hair cycle. Regardless of whether the trypsin blocked a survival signal or activated a death receptor to induce this process, this Example suggested that the configuration of the trypsin molecule might also have been responsible for the induction of programmed cell death and apoptosis in the follicular papillae.

Example 12

Use of Trypsin-Containing Composition

Glycerol dilaurate/cholesterol/polyoxyethylene-10-stearyl ether liposomes are prepared in accordance with the procedures set forth in Niemiec, wherein the constituent compounds of the liposomes are in a ratio of about 58:15:27, respectively.

After cooling the resulting liposomes to a temperature of about 40° C., the liposomes are added with normal mixing to an amount of a thickening agent composed of polyacrylamide (and) C13–C14 isoparaffin (and) laureth-7, available from Seppic, Inc. under the trade name "SEPIGEL 305," such that the amount of the thickening agent in the final composition is about 1–3% (w/v).

A sufficient amount of trypsin is then added thereto to produce a 1% trypsin (w/v) composition. This composition is appropriate for immediate topical application.

The resulting product possesses characteristics and properties of an effective shaving gel.

We claim:

1. A method for delaying mammalian hair growth comprising:
   topically applying to a surface of the skin of a mammal an effective amount of a topically active composition comprising a serine protease and a pharmaceutically or cosmetically acceptable vehicle comprising at least one liposome.

2. The method of claim 1 wherein the serine protease is trypsin.

3. The method of claim 1 wherein the serine protease is present in an amount, based upon the total volume of the topically active composition, of from about 0.00001% (w/v) to about 5% (w/v).

4. The method of claim 3 wherein the serine protease is present in an amount, based upon the total volume of the topically active composition, of from about 0.01% (w/v) to about 1% (w/v).

5. The method of claim 1 wherein hair growth is delayed for at least about 4 days.

6. The method of claim 1 wherein said at least one liposome is non-ionic.

7. The method of claim 6 wherein said at least one liposome is comprised of:
   a) glycerol dilaurate, glycerol distearate, or a mixture thereof;
   b) a compound having a steroid backbone as found in cholesterol; and
   c) a fatty acid ether having from about 12 to about 18 carbon atoms.

8. The method of claim 7 wherein the components of said at least one liposome are present in a ratio of about 53:10:22 to about 63:20:32, respectively.

9. The method of claim 6 wherein said at least one liposome is comprised of:
   a) glycerol dilaurate;
   b) cholesterol; and
   c) polyoxyethylene-1-stearyl ether.

10. The method of claim 1 wherein said pharmaceutically or cosmetically acceptable vehicle is present in an amount, based upon the total volume of said topically active composition, of from about 10 mg/ml to about 100 mg/ml.

11. The method of claim 1 wherein the serine protease is topically administered immediately before, immediately after or simultaneously with hair growth induction from telogen follicles.

12. The method of claim 11 wherein said serine protease is topically administered immediately after or simultaneously with hair growth induction from telogen follicles.

13. The method of claim 1 wherein the composition further comprises surfactants, moisturizers, humectants, conditioners, fragrances, colorants, or mixtures thereof.

14. The method of claim 13 wherein said composition is in the form of shaving creams, shaving gels, shaving powders, chemical depilatory creams, other products whose purpose is to either facilitate the removal of hair or actually remove hair or combinations thereof.

15. The method of claim 1 further comprising leaving said composition on said skin for a period sufficient to reduce hair growth.

16. The method of claim 15 wherein said period is at least about fifteen minutes.

17. The method of claim 1 wherein said composition further comprises a buffer comprising N-2-hydroxyethylpiperazine-N'-2-ethane sulfonic acid, (hydroxymethyl)aminomethane or mixtures thereof.

* * * * *